United States Patent [19]

Veber

[11] 4,115,554
[45] Sep. 19, 1978

[54] SOMATOSTATIN ANALOGS

[75] Inventor: Daniel F. Veber, Ambler, Pa.

[73] Assignee: Merck & Co., Inc., Rahway, N.J.

[21] Appl. No.: 828,791

[22] Filed: Aug. 29, 1977

[51] Int. Cl.² .................. A61K 37/02; C07C 103/52
[52] U.S. Cl. ........................... 424/177; 260/112.5 S
[58] Field of Search ................. 260/112.5 S; 424/177

Primary Examiner—Delbert R. Phillips
Attorney, Agent, or Firm—Walter Patton; Harry E. Westlake, Jr.

[57] ABSTRACT

Somatostatin analogs having the structural formula:

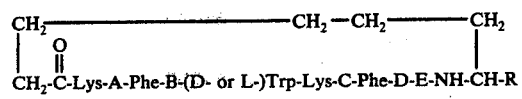

wherein
  R is H, COOH,
  A is $(Asn)_n$, α-Abu, Pro, Ala wherein n = 0 or 1,
  B is Phe, Tyr,
  C and D are independently Thr, Val,
  E is Ser, Pro, Ala, Gly, wherein at least one of A and E is Pro and the ring formed by the peptide backbone contains 35 to 38 atoms and pharmaceutically acceptable non-toxic acid addition salts thereof are prepared by the solid phase method. These peptides have the property of inhibiting the release of insulin, glucagon and growth hormone and decreasing gastric secretion in humans and animals. The compounds are particularly useful in the treatment of diabetes and gastric ulcers.

5 Claims, No Drawings

SOMATOSTATIN ANALOGS

BACKGROUND OF THE INVENTION

Somatostatin is a tetradecapeptide having the structure:

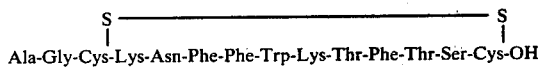

and has the properties of inhibiting the release of growth hormone, inhibiting the release of insulin and glucagon and reducing gastric secretion. Somatostatin itself has a short duration of action because it is inactivated, inter alia, by aminopeptidases and carboxypeptidases present in vivo. This problem of the short duration of action has been partially solved in the prior art by preparing derivatives of somatostatin which have low solubility, thus attaining a slow release on subcutaneous injection. Once dissolved, however, the derivatives are no more stable to inactivation by aminopeptidases and carboxypeptidases than somatostatin itself. The present invention provides somatostatin analogs having higher biological activities and a longer duration of action than somatostatin and a novel method for preparing said analogs.

SUMMARY OF THE INVENTION

This invention is concerned with novel somatostatin analogs having a more potent biological activity and a longer duration of action than naturally occurring somatostatin having the structural formula:

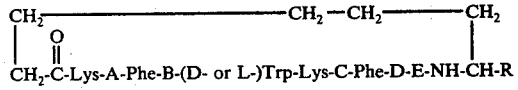

wherein
R is H, COOH,
A is (Asn)$_n$, α-Abu, Pro, Ala wherein $n = 0$ or 1,
B is Phe, Tyr,
C and D are independently Thr, Val,
E is Ser, Pro, Ala or Gly,
wherein at least one of A and E is Pro and the ring formed by the peptide backbone contains 35 to 38 atoms and pharmaceutically acceptable non-toxic acid addition salts thereof.

The preferred somatostatin analogs of the present invention are illustrated by the following structural formula:

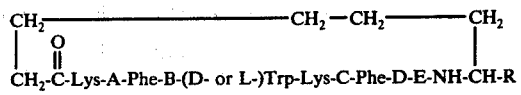

wherein
R is H,
A is Asn, Pro,
B is Phe,
C and D are Thr,
E is Ser, Pro
and wherein at least one of A and E is Pro and the pharmaceutically acceptable non-toxic acid addition salts thereof.

Still further preferred somatostatin analogs are those having the structural formulas:

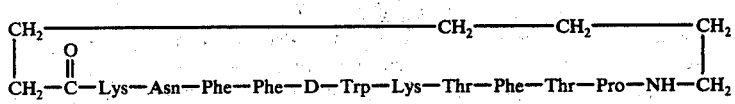

and

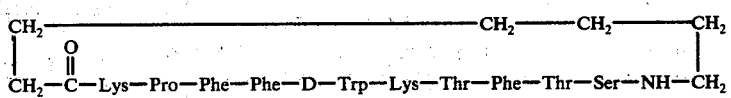

and the pharmaceutically acceptable non-toxic acid addition salts thereof.

Illustrative of acid addition salts are hydrochloride, hydrobromide, sulfate, phosphate, maleate, acetate, citrate, benzoate, succinate, malate, ascorbate and the like. The acid addition salts can be conveniently prepared by dissolving the above novel compounds in water, adding two equivalents of appropriate acid and freeze drying.

The somatostatin analogs of the present invention differ from somatostatin by virtue of the fact that at least one of positions 5 and 13 is substituted with Pro. Peptidases are believed to preferentially cleave peptide amide bonds wherein the amide is formed from a primary amino acid, i.e., only one substituent on the α-nitrogen atom such as Phe and Ser. Peptide amide bonds wherein the amide is formed from a secondary amino acid, i.e., proline, are resistant to cleavage by peptidases. Accordingly, the present invention provides novel active somatostatin analogs which have prolonged activity and increased potency believed to be due to resistance to peptidases. Furthermore, the present novel somatostatin analogs lack an N-terminal amino group thus eliminating the group involved in enzymic cleavage of the molecule by aminopeptidases. Furthermore, the deletion of the adjacent heteroatoms of the disulfide bridge of somatostatin increases the stability of the analogs in vivo by slowing down enzymatic degradation by reductive cleavage. Therefore, the analogs of the present invention are more resistant to cleavage in vivo than somatostatin and thus have a prolonged duration of action.

Somatostatin is a tetradecapeptide having the structure:

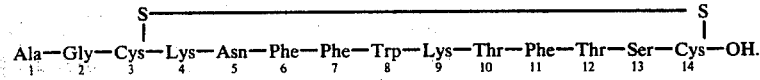

The portion of somatostatin extending from amino acid Cys$^3$ to Cys$^{14}$ forms a dodecapeptide of the following structure:

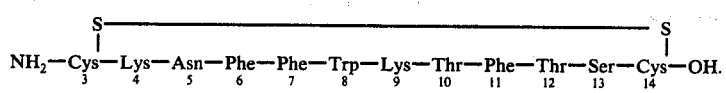

NH$_2$—Cys$_3$—Lys$_4$—Asn$_5$—Phe$_6$—Phe$_7$—Trp$_8$—Lys$_9$—Thr$_{10}$—Phe$_{11}$—Thr$_{12}$—Ser$_{13}$—Cys$_{14}$—OH.

The peptide backbone and the disulfide bridge form a 38 atom ring.

The present invention includes somatostatin analogs wherein the Ala$^1$-Gly$^2$ and the amino group of Cys$^3$ are deleted. Furthermore, the disulfide atoms of the cystine, -S-S-, have been replaced by the dicarba group, —CH$_2$—CH$_2$—. Whereas, in somatostatin positions 3 and 14 are bridged by cystine, the present invention provides somatostatin analogs wherein positions 3 and 14 are bridged by 7-aminoheptanoic acid or D- or L- α-aminosuberic acid. Furthermore, the somatostatin analogs of the present invention include those wherein Asn$^5$ is deleted or replaced by α-aminobutyric acid, Pro or Ala; Phe$^7$ is replaced by Tyr; Trp$^8$ is replaced by D-Trp and Thr$^{10\ and\ 12}$ are independently replaced by Val; and Ser$^{13}$ is replaced by Pro, Ala or Gly.

The abbreviated designations, which are used herein for the amino acid components, certain preferred protecting groups, reagents and solvents employed in the process of this invention are as follows:

TABLE I

| Abbreviated Designation | Amino Acid |
|---|---|
| Lys | L-lysine |
| Phe | L-phenylalanine |
| Trp | L-tryptophan |
| D-Trp | D-tryptophan |
| Thr | L-threonine |
| Aha | 7-aminoheptanoic acid |
| Tyr | L-tyrosine |
| Val | L-valine |
| Abu | L-α-aminobutyric acid |
| Ser | L-serine |
| Asn | L-asparagine |
| Pro | L-proline |
| Asu | D- or L-α-aminosuberic acid |

| Abbreviated Designation | Protecting Groups |
|---|---|
| INOC | isonicotinyloxycarbonyl |
| BOC | tert-butyloxycarbonyl |
| OMe | methyl ester |
| tBu | tert-butyl |
| CBZ | benzyloxycarbonyl |
| Bzl | benzyl |
| 2-Cl-CBZ | 2-chlorobenzyloxycarbonyl |

| Abbreviated Designation | Activating Groups |
|---|---|
| ONp | p-nitrophenyl ester |
| HSE | N-hydroxysuccinimide ester |
| HBT | 1-hydroxybenzotriazole |

| Abbreviated Designation | Condensing Agents |
|---|---|
| DCCI | dicyclohexylcarbodiimide |

TABLE I-continued

| Abbreviated Designation | Reagents |
|---|---|
| TFA | trifluoroacetic acid |
| TEA | triethylamine |
| DIPEA | diisopropylethylamine |

| Abbreviated Designation | Solvents |
|---|---|
| EPAW | ethyl acetate-pyridine-acetic acid-water |
| BAW | butanol-acetic acid-water |
| CMW | chloroform-methanol-water |
| DMF | dimethylformamide |
| THF | tetrahydrofuran |

In accordance with the present invention, the novel somatostatin analogs are prepared by cyclizing corresponding linear peptides. The linear peptides are prepared by using the solid phase sequential synthesis technique. Accordingly, the process for preparing the somatostatin analogs of the present invention comprises a) preparing a corresponding blocked linear peptide attached to a solid phase resin; b) selectively deblocking the N-terminal amine group; c) removing the linear peptide from the resin; d) treating the linear peptide with a cyclizing agent to obtain the cyclic peptide; and e) removing the remaining blocking groups.

When the linear peptide is prepared on the resin, it is not critical which amino acid is selected to be at the C-terminal position provided only that the sequence of amino acids in the linear peptide corresponds to that in the desired somatostatin analog. Once a linear peptide has been cyclized one can no longer determine which amino acid was at the C-terminus of the linear peptide. As an example to illustrate this, either of the two following linear peptides, when cyclized, will give the identical somatostatin analog:

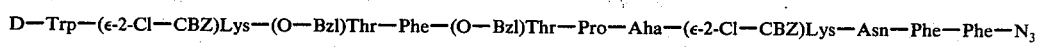

D—Trp—(ε-2-Cl—CBZ)Lys—(O—Bzl)Thr—Phe—(O—Bzl)Thr—Pro—Aha—(ε-2-Cl—CBZ)Lys—Asn—Phe—Phe—N$_3$ or

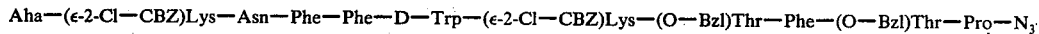

Aha—(ε-2-Cl—CBZ)Lys—Asn—Phe—Phe—D—Trp—(ε-2-Cl—CBZ)Lys—(O—Bzl)Thr—Phe—(O—Bzl)Thr—Pro—N$_3$.

↓ cyclization

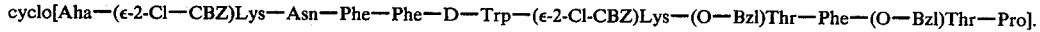

cyclo[Aha—(ε-2-Cl—CBZ)Lys—Asn—Phe—Phe—D—Trp—(ε-2-Cl-CBZ)Lys—(O—Bzl)Thr—Phe—(O—Bzl)Thr—Pro].

It is evident that since the linear peptide is going to be cyclized, it does not matter which amino acid is used to start the chain. Starting with Phe at the carboxyl end, as illustrated in the first of the two examples above, has an advantage over the second example. In the first example, D-Trp, which can react with t-butyl carbonium ions formed when BOC groups are removed, is the N-terminal amino acid and thus will be added last and hence will be subjected to the least amount of exposure to t-butyl carbonium ion.

In the case wherein R is COOH, it is preferable to employ the peptide having the amino acid sequence in the second example with the exception that Aha is replaced by ω-Asu. The process for preparing the required linear peptide may be illustrated by the following scheme:

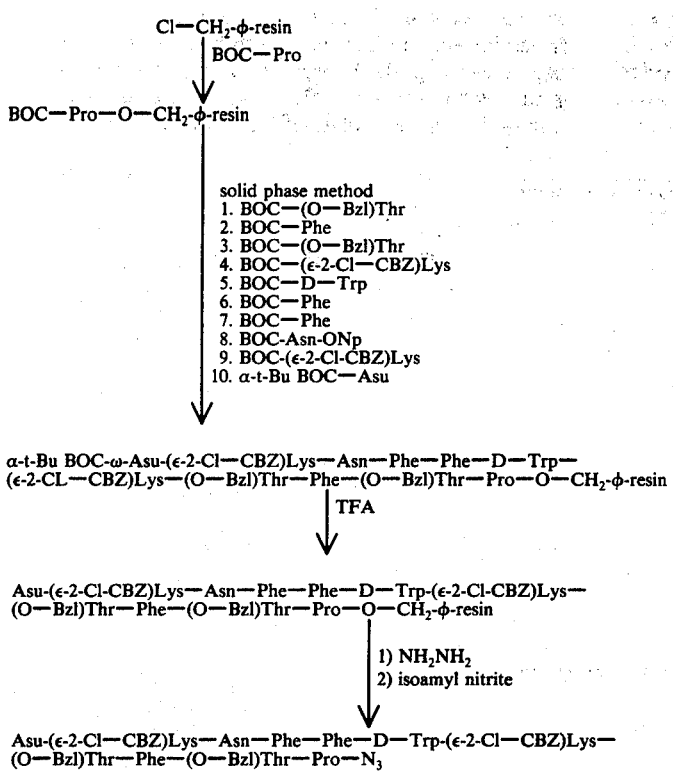

The synthesis of the linear peptides by the solid phase technique is conducted in a stepwise manner on chloromethylated resin. The resin is composed of fine beads (20–70 microns in diameter) of a synthetic resin prepared by copolymerization of styrene with 1 to 2 percent divinylbenzene. The benzene rings in the resin are chloromethylated in a Friedel-Crafts reaction with chloromethyl methyl ether and stannic chloride. The Friedel-Crafts reaction is continued until the resin contains 0.5 to 5 mmoles of chlorine per gram of resin.

The amino acid selected to be the C-terminal amino acid of the linear peptide is converted to its amino protected derivative. The carboxyl group of the selected C-terminal amino acid is bound covalently to the insoluble polymeric resin support, as for example, as the carboxylic ester of the resin-bonded benzyl chloride present in chloromethyl-substituted polystyrene-divinylbenzene resin. After the amino protecting group is removed, the amino protected derivative of the next amino acid in the sequence is added along with a coupling agent, such as dicyclohexylcarbodiimide. The amino acid reactant may be employed in the form of a carboxyl-activated amino acid such as the ONp ester, an amino acid azide, and the like. Deprotection and addition of successive amino acids is performed until the desired linear peptide is formed.

The selection of protecting groups is, in part, dictated by particular coupling conditions, in part by the amino acid and peptide components involved in the reaction.

Amino-protecting groups ordinarily employed include those which are well known in the art, for example, urethane protecting substituents such as benzyloxycarbonyl (carbobenzoxy), p-methoxycarbobenzoxy, p-nitrocarbobenzoxy, t-butyloxycarbonyl, and the like. It is preferred to utilize t-butyloxycarbonyl (BOC) for protecting the α-amino group in the amino acids undergoing reaction at the carboxyl end of said amino acid.

The BOC protecting group is readily removed following such coupling reaction and prior to the subsequent step by the relatively mild action of acids (i.e., trifluoro acetic acid, or hydrogen chloride in ethyl acetate).

The -OH group of Thr and Ser can be protected by the Bzl group and the ε-amino group of Lys can be protected by the INOC group or the 2-chlorobenzyloxycarbonyl (2-Cl-CBZ) group. In the case of Lys, it is preferred to protect the ε-amino group with 2-Cl-CBZ group as this group is removed simultaneously with the Bzl groups by treatment with HF after the linear peptide has been cyclized. The INOC group is not removed by HF and requires an additional treatment with Zn or catalytic hydrogenation. Neither group is affected by TFA, used for removing BOC protecting groups.

After the linear peptide has been formed on the solid phase resin, it may be removed from the resin by a variety of methods which are well known in the art. For example, the peptide may be cleaved from the resin with hydrazine and thus directly form the peptide hydrazide which may be subsequently cyclized, via the azide, to the desired cyclic peptide. The hydrazide is converted to the corresponding azide by reaction with a reagent which furnishes nitrous acid in situ. Suitable reagents for this purpose include a lower alkyl nitrite (e.g. t-butyl nitrite, isoamyl nitrite) or an alkali metal nitrite salt (e.g., sodium nitrite, potassium nitrite) in the presence of a strong acid such as hydrochloric, phosphoric, sulfonic, etc. This reaction is carried out in the presence of either water and/or a non-aqueous solvent such as dimethylformamide, tetrahydrofuran, dioxane, chloroform, methylene chloride, etc., at a temperature between about −40° C. and +20° C. Alternatively, the peptide may be removed from the resin by treatment with a lower alcohol such as methanol in the presence of an organic base such as triethylamine, thus resulting in the formation of the corresponding lower alcohol ester of the linear undecapeptide. The resulting ester may be converted to the hydrazide which may then be cyclized, via the azide, to the desired cyclic peptide. The preferred method for cleaving the peptide from the resin in the present invention is the use of hydrazine.

peptide has been prepared, the N-terminal amino group is selectively deblocked and the peptide is removed from the resin by treatment with hydrazine. The resulting linear peptide hydrazide with N-terminal amino group deblocked having the amino acid sequence: D-Trp-(ε-2-Cl-CBZ)Lys-(O-Bzl)Thr-Phe-(O-Bzl)Thr-

TABLE II
General Scheme for Preparing Cyclo(Aha—Lys—Asn—Phe—Phe—D—Trp—Lys—Thr—Phe—Thr—Pro)

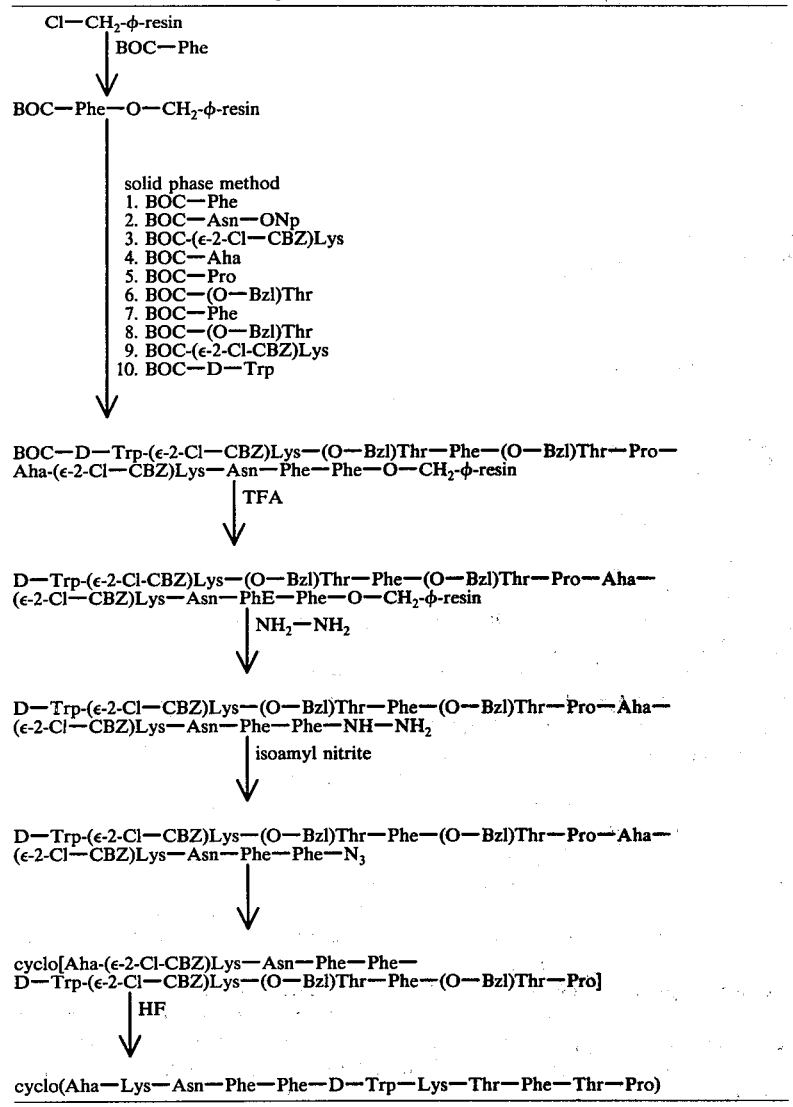

As reference to Table II will show, one preferred overall procedure for preparing the desired cyclic peptides of the present invention involves the stepwise synthesis of the linear peptide on a solid phase resin. More specifically, in the process for preparing cyclo(Aha-Lys-Asn-Phe-Phe-D-Trp-Lys-Thr-Phe-Thr-Pro), the carboxyl end of the N-blocked amino acid phenylalanine is bound covalently to an insoluble polymeric resin support as the carboxylic acid ester of the resin-bonded benzyl chloride. The amino group of Phe is protected by the BOC group. After the attachment of the Phe is completed on the resin, the protecting group BOC is removed by treatment with TFA in $CH_2Cl_2$. The subsequent amino acids are attached, in the form of BOC-amino acid, using DCCI as the condensing agent or an active ester such as ONp. After the desired linear Pro-Aha-(ε-2-Cl-CBZ)Lys-Asn-Phe-Phe-NH-$NH_2$ is treated with isoamyl nitrite in acid pH to form the corresponding azide. The azide solution is diluted with solvent and neutralized with an organic base. The linear peptide cyclizes to form cyclo-[Aha-(ε-2-Cl-CBZ)Lys-Asn-Phe-Phe-D-Trp-(ε-2-Cl-CBZ)Lys-(O-Bzl)Thr-Phe-(O-Bzl)Thr-Pro]. During the cyclization the "pH" is checked and maintained at neutral by the addition of organic base. The "pH" in organic solvent is determined by the application of an aliquot of the solution to moistened narrow range pH paper.

After the linear peptide is cyclized, the remaining protective groups, 2-Cl-CBZ and Bzl, are removed in one step by treatment with HF in the presence of anisole. The crude cyclic peptides obtained by the processes of Table II are purified by chromatography, preferably on Sephadex eluted with 50% aqueous acetic acid.

The following Examples illustrate methods of carrying out the present invention, but is to be understood that these Examples are given for purposes of illustration and not of limitation. It is to be understood that changing the amino acid sequence of the polypeptide in accordance with the instructions provided by this disclosure, affords each of the compounds embraced by the description presented herein and embraced by the claims of this application.

EXAMPLE 1

Preparation of
Cyclo(Aha-Lys-Asn-Phe-Phe-D-Trp-Lys-Thr-Phe-Thr-Pro)

Step a) — Preparation of BOC-D-Trp-($\epsilon$-2-Cl-CBZ)Lys-(O-Bzl)Thr-Phe-(O-Bzl)Thr-Pro-Aha-($\epsilon$-2-Cl-CBZ)Lys-Asn-Phe-Phe-O-$CH_2$-$\phi$-resin which case the coupling was carried out in the presence of DCCI and 1-hydroxybenzotriazole monohydrate ($HBT.H_2O$).

The coupling of each amino acid proceeded smoothly. Best yields were obtained when the coupling was repeated in each step. When the coupling as repeated, the initial two chloroform washes, the deblocking step and the succeeding three chloroform washes were all omitted and replaced by a single chloroform wash.

The coupling reactions were carried out in methylene chloride, freshly degassed DMF or a mixture of these two solvents. The N-terminal amino group was blocked with a BOC group in each case; the hydroxy group of Thr was blocked with Bzl and the $\epsilon$-amino group of Lys with 2-Cl-CBZ.

When the desired BOC-undecapeptide-O-$CH_2$-$\phi$-resin was obtained, the N-terminal BOC group was removed by the terminal deblocking procedure set forth in Table V.

TABLE III

| Solvent or reagent (number of treatments or washes) | $CHCl_3$ (2) | 25% TFA in $CH_2Cl_2$ (2) | $CHCl_3$ (3) | $NEt_3$ $CH_2Cl_2$ (1:9) (2) | $CHCl_3$ (3) $CH_2Cl_2$ (3) * | BOC AA in $CH_2Cl_2$, DMF or a mixture of both | 0.5M DCCI in $CH_2Cl_2$ ** | DMF (1) MeOH (1) DMF (1) MeOH (1) $CHCl_3$ (2) |
|---|---|---|---|---|---|---|---|---|
| Volume in ml | 40 | 40 | 40 | 40 | 40 | 25 ml. | 10 | 40 |
| Time in min. | 5 | 2 and 25 | 2 | 5 and 5 | 2 | 5 | 5 min. coupling 30 min. | 2 |

*When BOC Active Ester Coupling is employed: DMF (3) washes substituted for $CH_2Cl_2$.
**When BOC Active Ester Coupling is employed: No DCCI is added and coupling time is 600 min.

Chloromethyl resin (2% cross-linked Merrifield resin), 862.0 g. (2.37 moles), having 2.75 meq. chlorine/g., and 607.0 g. (2.37 moles, 1 equivalent) of BOC-Phe were added to 4320 ml. of peroxide-free tetrahydrofuran. The mixture was stirred in an oil bath at 80° C. bath temperature for 45 minutes. Triethylamine, 310.0 ml., was added and the reaction mixture stirred at 80° C. bath temperature for 70 hours, cooled to 25° C. and transferred to a stirred solid phase reaction column with 2000 ml. of tetrahydrofuran. After removal of the solvent, the resin was washed using the stirred column with:

3 × 2000 ml. of tetrahydrofuran
4 × 5170 ml. of ethanol
1 × 5170 ml. of acetic acid
3 × 5170 ml. of water
3 × 5170 ml. of methanol
3 × 5170 ml. of chloroform.

The BOC-Phe-O-$CH_2$-$\phi$-resin was dried in vacuo at 25° C. for 16 hours, giving 1203 g. of BOC-Phe-O-$CH_2$-$\phi$-resin containing 0.937 mmole of phenylalanine/g. of resin.

BOC-Phe-O-$CH_2$-$\phi$-resin (2.13 g.; 2.0 mmole) was carried through the procedure in Tables III and IV using 2 deblockings (2 minutes and 25 minutes) with 25% TFA in methylene chloride, and 2.5 equivalents of BOC-amino acid in the required sequence until the desired BOC-undecapeptide-O-$CH_2$-$\phi$-resin was obtained.

In the coupling of BOC-Asn to Phe-Phe-O-$CH_2$-$\phi$-resin, in place of BOC-AA, the p-nitrophenyl ester of BOC-Asn, (BOC-Asn-ONp), was used and the DCCI was omitted.

DCCI was used as the sole coupling agent in every remaining step except the coupling of BOC-Pro to Aha-($\epsilon$-2-Cl-CBZ)Lys-Asn-Phe-Phe-O-$CH_2$-$\phi$-resin in

TABLE IV

| Protected Amino Acid | Solvent ml. |
|---|---|
| BOC-Phe (1.33 g.) recouple | $CH_2Cl_2$, 25 ml. |
| BOC-Asn-ONp (1.77 g.) recouple | DMF, 25 ml. |
| BOC-($\epsilon$-2-Cl-CBZ)Lys (2.08 g.) recouple | $CH_2Cl_2$, 25 ml. |
| BOC-Aha (1.23 g.) recouple | $CH_2Cl_2$, 25 ml. |
| BOC-Pro (1.08 g.) + $HBT.H_2O$ (1.53 g.) recouple | DMF, 25 ml. |
| BOC-(O-Bzl)Thr (1.55 g.) recouple | $CH_2Cl_2$, 25 ml. |
| BOC-Phe (1.33 g.) recouple | $CH_2Cl_2$, 25 ml. |
| BOC-(O-Bzl)Thr (1.55 g.) recouple | $CH_2Cl_2$, 25 ml. |
| BOC-($\epsilon$-2-Cl-CBZ)Lys (2.08 g.) recouple | $CH_2Cl_2$, 25 ml. |
| BOC-D-Trp (1.52 g.) recouple | DMF, 5.5 ml. $CH_2Cl_2$, 19.5 ml. |

TABLE V

TERMINAL DEBLOCKING PROGRAM

| Solvent or reagent (number of treatments or washes) | $CHCl_3$ (1) | 25% TFA in $CH_2Cl_2$ + 1% Ethanedithiol (2) | $CHCl_3$ (3) | MeOH (2) $CH_2Cl_2$ (1) MeOH (2) $CH_2Cl_2$ (2) |
|---|---|---|---|---|
| Vol. in ml. | 40 | 40 | 40 | 40 |
| Time in minutes | 5 | 2 and 25 | 2 | 2 |

After the sequence of Tables III, IV and V were completed, the blocked undecapeptide-O-$CH_2$-$\phi$-resin was dried overnight in vacuo and weighed 5.41 g.

Step b) — Preparation of D-Trp-(ε-2-Cl-CBZ)Lys-(O-Bzl)Thr-Phe-(O-Bzl)Thr-Pro-Aha-(ε-2-Cl-CBZ)Lys-Asn-Phe-Phe-NH-NH$_2$ to a mixture of 5.24 g. D-Trp-(ε-2-Cl-CBZ)Lys-(O-Bzl)Thr-Phe-(O-Bzl)Thr-Pro-Aha-(ε-2-Cl-CBZ)Lys-Asn-Phe-Phe-O-CH$_2$-φ-resin in 60 ml. freshly degassed DMF was added 5.0 ml. NH$_2$-NH$_2$. The mixture was magnetically stirred at room temperature for 1 hour. The mixture was filtered to remove the resin. The resin was washed with 4 × 30 ml. DMF. The filtrate and washings were concentrated in vacuo to near dryness. The semi-solid residue was triturated with 60 ml. ether to obtain a solid. The solid was collected by filtration, slurried with ether 3 × 20 ml. and dried in vacuo for 20 min. to yield 3.89 g. crude product. The solid was slurried with 4 × 30 ml. water to remove all traces of formylhydrazide and dried in vacuo overnight to give 3.02 g. of product.

Step c) — Preparation of D-Trp-(ε-2-Cl-CBZ)Lys-(O-Bzl)Thr-Phe-(O-Bzl)Thr-Pro-Aha-(ε-2-Cl-CBZ)Lys-Asn-Phe-Phe-N$_3$ D-Trp-(ε-2-Cl-CBZ)Lys-(O-Bzl)Thr-Phe-(O-Bzl)Thr-Pro-Aha-(ε-2-Cl-CBZ)Lys-Asn-Phe-Phe-NH-NH$_2$ (2.90 g., 1.47 mmole), prepared by the process set forth in Step b), was suspended in 30 ml. freshly degassed DMF. The suspension was stirred magnetically at −40° C. under a nitrogen atmosphere. To the suspension was added 1.53 ml., 6.15N HCl in THF (9.41 mmole, 6.4 equivalents). The resulting clear acidic solution, "pH" 1.0 to 1.5, was warmed to −25° C. and 0.30 ml. isoamyl nitrite (0.135 ml./mmole, 1.5 equivalents) was added and stirring continued for 30 minutes. This solution of D-Trp-(ε-2-Cl-CBZ)Lys-(O-Bzl)Thr-Phe-(O-Bzl)Thr-Pro-Aha-(ε-2-Cl-CBZ)Lys-Asn-Phe-Phe-N$_3$ was used immediately in Step d).

Step d) — Preparation of Cyclo[Aha-(ε-2-Cl-CBZ)Lys-Asn-Phe-Phe-D-Trp-(ε-2-Cl-CBZ)Lys-(O-Bzl)Thr-Phe-(O-Bzl)Thr-Pro]

The solution of D-Trp-(ε-2-Cl-CBZ)Lys-(O-Bzl)Thr-Phe-(O-Bzl)Thr-Pro-Aha-(ε-2-Cl-CBZ)Lys-Asn-Phe-Phe-N$_3$ in DMF, obtained by the process set forth in Step c), was diluted in 1800 ml. freshly degassed DMF, precooled to −40° C. The solution was maintained under a nitrogen atmosphere and allowed to warm to −20° C. during which time the "pH" was maintained at 7.2 to 7.6 by the addition of 3.06 ml. N,N-diisopropylethylamine. The solution was maintained at −18° C. for 24 hours and then kept at 5° C. for an additional 3 days.

The solution was concentrated in vacuo to a thick oil, washed twice with ether and once with ethyl acetate and triturated with water to give a solid. The solid was collected by filtration and dried in vacuo overnight to give 2.06 g. of product.

Step e) — Preparation of Cyclo(Aha-Lys-Asn-Phe-Phe-D-Trp-Lys-Thr-Phe-Thr-Pro)

Cyclo[Aha-(ε-2-Cl-CBZ)Lys-Asn-Phe-Phe-D-Trp-(ε-2-Cl-CBZ)Lys-(O-Bzl)Thr-Phe-(O-Bzl)Thr-Pro], 2.0 g., obtained by the process set forth in Step d), was dissolved in 3 ml. anisole and 30 ml. hydrogen fluoride at dry ice-acetone bath temperature. The solution was stirred magnetically at ice-bath temperature for 1 hour. The excess hydrogen fluoride was removed in vacuo at ice-bath temperature. The resulting oily residue was triturated with ethyl acetate to give a solid. The solid was collected by filtration, washed with ethyl acetate and dried in vacuo to give 1.48 g. of product.

Step f) — Purification of Cyclo(Aha-Lys-Asn-Phe-Phe-D-Trp-Lys-Thr-Phe-Thr-Pro)

The cyclo(Aha-Lys-Asn-Phe-Phe-D-Trp-Lys-Thr-Phe-Thr-Pro), 1.20 g., obtained by the process set forth in Step e), was dissolved in 25 ml. 50% aqueous acetic acid and charged to a column of Sephadex G-50, (fine) (5 cm. × 115 cm., 2260 ml.) packed in 50% aqueous acetic acid. The column was eluted with 50% aqueous acetic acid at the rate of 17 ml./10 min./fraction. The effluent was monitored at 280 nm.

Fractions 105 to 115 were combined, concentrated to dryness in vacuo and the residue lyophilized from 20 ml. 10% aqueous acetic acid to give 648 mg. of substantially pure product. A 20 hour acid hydrolysate showed the following amino acid analysis:

|  | μmole/mg. | normalized to average |
|---|---|---|
| Lys | 1.05 | 1.98 |
| Asp | 0.571 | 1.08 |
| Thr | 1.07 | 2.02 |
| Pro | 0.533 | 1.01 |
| Phe | 1.54 | 2.91 |
| Trp (by U.V.) | 0.530 | 1.00 |

EXAMPLE 2

Preparation of Cyclo(Aha-Lys-Pro-Phe-Phe-D-Trp-Lys-Thr-Phe-Thr-Ser)

Step a) — Preparation of D-Trp-(ε-2-Cl-CBZ)Lys-(O-Bzl)Thr-Phe-(O-Bzl)Thr-(O-Bzl)Ser-Aha-(ε-2-Cl-CBZ)Lys-Pro-Phe-Phe-O-CH$_2$-φ-resin Chloromethyl resin (2% cross-linked Merrifield resin), 862.0 g. (2.37 moles), having 2.75 meq. chlorine/g., and 607.0 g. (2.37 moles, 1 equivalent) of BOC-Phe were added to 4320 ml. of peroxide-free tetrahydrofuran. The mixture was stirred in an oil bath at 80° C. bath temperature for 45 minutes. Triethylamine, 310.0 ml., was added and the reaction mixture stirred at 80° C. bath temperature for 70 hours, cooled to 25° C. and transferred to a stirred solid phase reaction column with 2000 ml. of tetrahydrofuran. After removal of the solvent, the resin was washed using the stirred column with:

3 × 2000 ml. of tetrahydrofuran
4 × 5170 ml. of ethanol
1 × 5170 ml. of acetic acid
3 × 5170 ml. of water
3 × 5170 ml. of methanol
3 × 5170 ml. of chloroform.

The BOC-Phe-O-CH$_2$-φ-resin was dried in vacuo at 25° C. for 16 hours, giving 1203 g. of BOC-Phe-O-CH$_2$-φ-resin containing 0.937 mmole of phenylalanine/g. of resin.

BOC-Phe-O-CH$_2$-φ-resin (2.31 g.; 2.0 mmole) was carried through the procedures in Tables III of Example 1 and Table VI using 2 deblockings (2 minutes and 25 minutes) with 25% TFA in methylene chloride, and 2.5 equivalents of BOC-amino acid in the required sequence until the desired BOC-undecapeptide-O-CH$_2$-φ-resin was obtained.

DCCI was used as the coupling agent in every step. The coupling of each amino acid proceeded smoothly.

Best yields were obtained when the coupling was repeated in each step. When the coupling was repeated, the initial two chloroform washes, the deblocking step and the succeeding three chloroform washes were all omitted and replaced by a single chloroform wash.

The coupling reactions were carried out in methylene chloride, or a mixture of freshly degassed DMF and methylene chloride. The N-terminal amino group was blocked with a BOC group in each case; the hydroxy group of Thr and Ser was blocked with Bzl and the $\epsilon$-amino group of Lys with 2-Cl-CBZ.

When the desired BOC-undecapeptide-O-CH$_2$-$\phi$-resin was obtained, the N-terminal BOC group was removed by the terminal deblocking procedure set forth in Table V of Example 1.

TABLE VI

| Protected Amino Acid | Solvent ml. |
| --- | --- |
| BOC-Phe (1.33 g.) recouple | CH$_2$Cl$_2$, 25 ml. |
| BOC-Pro (1.08 g.) recouple | CH$_2$Cl$_2$, 25 ml. |
| BOC-($\epsilon$-2-Cl-CBZ)Lys (2.08 g.) recouple | CH$_2$Cl$_2$, 25 ml. |
| BOC-Aha (1.23 g.) recouple | CH$_2$Cl$_2$, 25 ml. |
| BOC-(O-Bzl)Ser (1.48 g.) recouple | CH$_2$Cl$_2$, 25 ml. |
| BOC-(O-Bzl)Thr (1.55 g.) recouple | CH$_2$Cl$_2$, 25 ml. |
| BOC-Phe (1.33 g.) recouple | DMF, 25 ml. |
| BOC-(O-Bzl)Thr (1.55 g.) recouple | CH$_2$Cl$_2$, 25 ml. |
| BOC-($\epsilon$-2-Cl-CBZ)Lys (2.08 g.) recouple | CH$_2$Cl$_2$, 25 ml. |
| BOC-D-Trp (1.52 g.) recouple | DMF, 5.5 ml. CH$_2$Cl$_2$, 19.5 ml. |

After the sequence of Tables III, V and VI were completed, the blocked undecapeptide-O-CH$_2$-$\phi$-resin dried overnight in vacuo and weighed 5.30 g.

An acid hydrolysate showed the following amino acid composition:

|  | μmole/mg. | normalized to average |
| --- | --- | --- |
| Lys | 0.627 | 1.84 |
| Thr | 0.511 | 1.5 |
| Ser | 0.207 | 0.61 |
| Pro | 0.337 | 0.99 |
| Phe | 1.02 | 3.00 |

Step b) — Preparation of D-Trp-($\epsilon$-2-Cl-CBZ)Lys-(O-Bzl)Thr-Phe-(O-Bzl)Thr-(O-Bzl)Ser-Aha-($\epsilon$-2-Cl-CBZ)Lys-Pro-Phe-Phe-NH-NH$_2$ To a mixture of 5.0 g. D-Trp-($\epsilon$-2-Cl-CBZ)Lys-(O-Bzl)Thr-Phe-(O-Bzl)Thr-(O-Bzl)Ser-Aha-($\epsilon$-2-Cl-CBZ)Lys-Pro-Phe-Phe-O-CH$_2$-$\phi$-resin in 50 ml. freshly degassed DMF was added 5.0 ml. NH$_2$-NH$_2$. The mixture was magnetically stirred at room temperature for 55 minutes. The mixture was filtered to remove the resin. The filtrate and washings were concentrated in vacuo to an oily residue. The residue was triturated with ether and ethyl acetate to obtain a solid. The solid was collected by filtration and dried in vacuo. The solid was slurried, filtered and washed with water 8 × to remove formylhydrazide and dried in vacuo overnight to give 2.30 g. of product.

Step c) — Preparation of D-Trp-($\epsilon$-2-Cl-CBZ)Lys-(O-Bzl)Thr-Phe(O-Bzl)Thr-(O-Bzl)Ser-Aha-($\epsilon$-2-Cl-CBZ)Lys-Pro-Phe-Phe-N$_3$ D-Trp-($\epsilon$-2-Cl-CBZ)Lys-(O-Bzl)Thr-Phe-(O-Bzl)Thr-(O-Bzl)Ser-Aha-($\epsilon$-2-Cl-CBZ)Lys-Pro-Phe-Phe-NH-NH$_2$ (2.2 g., 1.08 mmole), prepared by the process set forth in step b), was dissolved in 40 ml. freshly degassed DMF. The solution was stirred magnetically at −25° C. To the solution was added 1.655 ml. of 5.72N HCl in THF (9.47 mmoles, 8.77 equivalents). To the resulting acidic solution, "pH" 1.0 to 1.5, was added 0.23 ml. isoamyl nitrite (1.7 mmoles, 1.576 equivalents) and stirring continued for 30 minutes at −25° C. and then cooled to −40° C. This solution of D-Trp-($\epsilon$-2-Cl-CBZ)Lys-(O-Bzl)Thr-Phe-(O-Bzl)Thr-(O-Bzl)Ser-Aha-($\epsilon$-2-Cl-CBZ)Lys-Pro-Phe-Phe-N$_3$ was used immediately in Step d).

Step d) — Preparation of Cyclo[(O-Bzl)Thr-(O-Bzl)-Ser-Aha-($\epsilon$-2-Cl-CBZ)Lys-Pro-Phe-Phe-D-Trp-($\epsilon$-2-Cl-CBZ)Lys-(O-Bzl)Thr-Phe]

The solution of D-Trp-($\epsilon$-2-Cl-CBZ)Lys-(O-Bzl)Thr-Phe-(O-Bzl)Thr-(O-Bzl)Ser-Aha-($\epsilon$-2-Cl-CBZ)Lys-Pro-Phe-Phe-N$_3$ in DMF, obtained by the process set forth in Step c), was diluted in 2000 ml. freshly degassed DMF, precooled to −40° C. The solution was maintained under a nitrogen atmosphere and allowed to warm to −20° C. during which time the "pH" was maintained at 7.2 to 7.6 by the addition of 3.2 ml. N,N-diisopropylethylamine. The solution was maintained at −18° C. for 24 hours and then kept at 5° C. for an additional 24 hours.

The solution was concentrated in vacuo to a thick oil, triturated once with a mixture of ether and petroleum ether, twice with ether, and once with a mixture of ethyl acetate and ether. The residue was dried and triturated with a total of 150 ml. water to give a solid. The solid was collected by filtration and dried in vacuo overnight to give 2.25 g. of product.

An acid hydrolysate showed the following amino acid composition:

|  | μmol/mg. | normalized to average |
| --- | --- | --- |
| Lys | 0.858 | 1.95 |
| Thr | 0.871 | 1.98 |
| Ser | 0.446 | 1.02 |
| Pro | 0.450 | 1.03 |
| Phe | 0.450 | 1.03 |
| Trp | 0.089 | 0.20 |

Step e) — Preparation of Cyclo(Aha-Lys-Pro-Phe-Phe-D-Trp-Lys-Thr-Phe-Thr-Ser)

Cyclo[(O-Bzl)Thr-(O-Bzl)Ser-Aha-($\epsilon$-2-Cl-CBZ)Lys-Pro-Phe-Phe-D-Trp-($\epsilon$-2-Cl-CBZ)Lys-(O-Bzl)Thr-Phe], 2.1 g., obtained by the process set forth in Step d), was dissolved in 3 ml. anisole and 30 ml. hydrogen fluoride at dry ice-acetone bath temperature. The solution was stirred magnetically at ice-bath temperature for 20 minutes. The excess hydrogen fluoride was removed in vacuo at ice-bath temperature. The resulting oily residue was maintained in vacuo for an additional 20 minutes at ice-bath temperature and triturated with ethyl acetate to give a solid. The solid was collected by filtration and dried in vacuo for 3 hours to give 1.44 g. of product.

Step f) — Purification of Cyclo(Aha-Lys-Pro-Phe-Phe-D-Trp-Lys-Thr-Phe-Thr-Ser)

The cyclo(Aha-Lys-Pro-Phe-Phe-D-Trp-Lys-Thr-Phe-Thr-Ser), 1.44 g., obtained by the process set forth in Step e), was divided into two equal portions. Each portion was dissolved in 10 ml. acetic acid to which was added 10 ml. water. The resulting cloudy solution was charged to a column of Sephadex G-50, (5 cm. × 115 cm., 2260 ml.) packed in 50% aqueous acetic acid. The column was eluted with 50% aqueous acetic acid at the rate of 17.2 ml./10 min./fraction. The effluent was monitored at 280 nm.

Fractions 96 to 107 from the first column and fractions 98 to 109 from the second column were combined, concentrated to dryness in vacuo and the residue lyophilized from 20 ml. 10% aqueous acetic acid to give 1.1155 g. of substantially pure product. A 20 hour acid hydrolysate showed the following amino acid analysis:

|     | μmole/mg. | normalized to average |
| --- | --- | --- |
| Lys | 1.18 | 2.03 |
| Thr | 1.11 | 1.91 |
| Ser | 0.597 | 1.03 |
| Pro | 0.611 | 1.05 |
| Phe | 1.74 | 2.99 |
| Trp | — | 0.95 (by U.V.) |

The somatostatin analogs of the present invention and the non-toxic pharmaceutically acceptable salts thereof, are useful in humans and animals for inhibiting growth hormone release as in the treatment of acromegaly. They are useful for inhibiting the release of glucagon and alone or in conjunction with insulin, for lowering blood glucose as in the treatment of diabetes. They inhibit the release of gastric secretions and are useful as in the treatment of gastric ulcers. In the treatment of diabetes, the number and size of daily doses and the time of administration are determined by an individual study of each subject. The method of determining these factors is known to those skilled in the art.

The somatostatin analogs described herein may be administered to warm blooded animals, including humans, either intravenously, subcutaneously, intramuscularly or orally. The contemplated dose range for oral administration in tablet or capsule form to large mammals is about 0.001 mg. to about 7 mg./kg. of body weight per day. These somatostatin analogs are preferably administered by injection. A therapeutically effective amount of an analog is ordinarily supplied at a dosage level of from about 0.001 mg. to about 2 mg./kg. of body weight. Preferably the range is from about 0.00142 mg. to about 0.428 mg./kg. of body weight administered by intravenous infusion or by subcutaneous injection. The required dosage will vary with the particular condition being treated, the severity of the condition and the duration of treatment.

If the active ingredient is administered in tablet form, the tablet may contain: a binder such as gum tragacanth, corn starch, gelatin, an excipient such as dicalcium phosphate; a disintegrating agent such as corn starch and alginic acid; a lubricant such as magnesium stearate; and a sweetening and/or flavoring agent such as sucrose, lactose and wintergreen. Suitable liquid carriers for intravenous administration include sterile water, isotonic saline and phosphate buffer solutions or other pharmaceutically acceptable injectable carriers.

The following example is included to illustrate the preparation of a representative dose of cyclo(Aha-Lys-Asn-Phe-Phe-D-Trp-Lys-Thr-Phe-Thr-Pro) suitable for subcutaneous injection.

EXAMPLE 3

1 ml. — sterile saline;
1 mg. — cyclo(Aha-Lys-Asn-Phe-Phe-D-Trp-Lys-Thr-Phe-Thr-Pro)

What is claimed is:

1. Compounds of the formula:

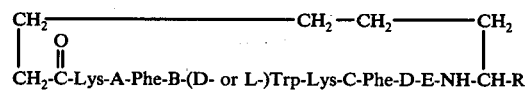

wherein
R is H, COOH,
A is (Asn)$_n$, α-Abu, Pro, Ala wherein $n = 0$ or 1,
B is Phe, Tyr,
C and D are independently Thr, Val,
E is Ser, Pro, Ala, Gly,
wherein at least one of A and E is Pro and the ring formed by the peptide backbone contains 35 to 38 atoms and pharmaceutically acceptable non-toxic acid addition salts thereof.

2. The compound according to claim 1 wherein
R is H,
A is Asn, Pro,
B is Phe,
C and D are Thr,
E is Ser, Pro
wherein at least one of A and E is Pro.

3. The compound according to claim 2 having the formula:

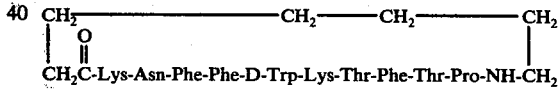

4. The compound according to claim 2 having the formula:

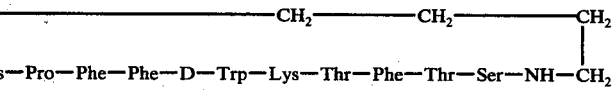

5. A composition comprising a therapeutically effective amount of the peptides having the structure:

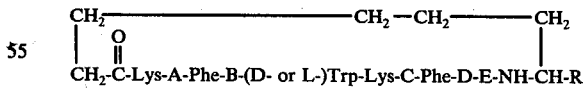

wherein
R is H, COOH,
A is (Asn)$_n$, α-Abu, Pro, Ala wherein $n = 0$ or 1,
B is Phe, Tyr,
C and D are independently Thr, Val,
E is Ser, Pro, Ala, Gly,
wherein at least one of A and E is Pro and the ring formed by the peptide backbone contains 35 to 38 atoms and pharmaceutically acceptable non-toxic acid addition salts thereof in a pharmaceutically acceptable excipient.

* * * * *